United States Patent
Farer et al.

(10) Patent No.: US 6,471,950 B1
(45) Date of Patent: Oct. 29, 2002

(54) NAIL ENAMEL COMPOSITION HAVING FLUOROSILANE COATED PARTICULARS

(75) Inventors: Alan Farer, Kinnelon; Christian Lee, Parsippany, both of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/465,606

(22) Filed: Dec. 17, 1999

(51) Int. Cl.[7] .............................. A61K 6/00; A61K 7/00; A61K 7/04
(52) U.S. Cl. ................... 424/61; 424/401; 514/772.6
(58) Field of Search .................... 424/401, 61; 556/482; 514/772.6

(56) References Cited

U.S. PATENT DOCUMENTS

| | | | |
|---|---|---|---|
| 4,166,110 A | 8/1979 | Isobe et al. | 424/61 |
| 4,229,227 A | 10/1980 | Ikeda et al. | 106/181 |
| 4,283,324 A | 8/1981 | Duffy | 260/31.2 N |
| 4,832,944 A | 5/1989 | Socci et al. | 424/61 |
| 5,066,484 A * | 11/1991 | Castrogiovanni et al. | 424/61 |
| 5,174,996 A * | 12/1992 | Weber et al. | 424/401 |
| 5,225,195 A | 7/1993 | Soyama et al. | 424/401 |
| 5,344,583 A | 9/1994 | Bayless | 252/171 |
| 5,458,976 A * | 10/1995 | Horino et al. | 428/405 |
| 5,482,547 A | 1/1996 | Bugnon et al. | 106/493 |
| 5,688,494 A | 11/1997 | Graves et al. | 424/61 |
| 5,766,332 A | 6/1998 | Graves et al. | 106/169.17 |
| 5,792,447 A | 8/1998 | Socci et al. | 424/61 |
| 5,863,523 A | 1/1999 | Socci et al. | 424/61 |

FOREIGN PATENT DOCUMENTS

| | | | |
|---|---|---|---|
| CA | 1276562 | | 11/1990 |
| JP | 402202941 | * | 8/1990 |
| JP | 408208418 | * | 9/1990 |
| JP | 7-53326 | | 2/1995 |
| JP | 7053326 | * | 2/1995 |

* cited by examiner

*Primary Examiner*—Thurman K. Page
*Assistant Examiner*—S. Howard
(74) *Attorney, Agent, or Firm*—Ohlandt, Greeley, Ruggiero & Perle, LLP

(57) ABSTRACT

A cosmetic composition for nail enamel having particulates, such as pigments and/or fillers, coated with fluorosilane is provided. The present invention also provides methods of (a) reducing settling, migration and floatation of colorants in a nail enamel, (b) reducing nail staining in a nail, (c) improving gloss of a nail enamel, and (d) increasing stability and improving rheology of a nail enamel.

20 Claims, No Drawings

NAIL ENAMEL COMPOSITION HAVING FLUOROSILANE COATED PARTICULARS

BACKGROUND OF THE INVENTION

1. Field of the Invention

The present invention relates to nail enamel compositions. More particularly, the present invention relates to nail enamel compositions having fluorosilane-coated particulates. The present invention further relates to methods for (a) reducing settling, migration and floatation of colorants in a nail enamel; (b) reducing staining on the nail; (c) improving gloss in a nail enamel; (d) improving or increasing water resistance or repellency in a nail enamel; (e) improving or increasing stability of a nail enamel; and (f) improving or increasing rheology of a nail enamel. These methods include applying topically to a person a nail enamel composition having colorant particulates coated with fluorosilane.

2. Description of the Prior Art

U.S. Pat. Nos. 5,863,523 and 5,792,447 to Socci et al.; U.S. Pat. Nos. 5,766,332 and 5,688,494 to Graves et al.; U.S. Pat No. 5,344,583 to Bayless; U.S. Pat. No. 5,225,195 to Soyama et al.; U.S. Pat. No. 5,174,996 to Weber et al.; U.S. Pat. No. 4,283,324 to Duffy; U.S. Pat. No. 4,229,227 to Ikeda et al.; and U.S.Pat. No. 4,166,110 to Isobe et al., and Canadian Patent No. 1,276,562 to Schnetzinger et al., are directed to nail enamel compositions.

U.S. Pat. No. 4,832,944 to Socci et al. is directed to a nail enamel containing an inorganic pigment coated with an organically substituted polysiloxane.

U.S. Pat. No. 5,482,547 to Bugnon et al. is directed to a paint or varnish containing an organic pigment coated with a silicate.

Japan Patent No. 7053326 is directed to a makeup cosmetic material that contains modified powder prepared by coating powder with methylhydrogensiloxane and heat-treating and blending modified powder coated with a fluorine containing compound.

Some cosmetic products, particularly cosmetic products having colored compositions, suffer from stability problems that lead to an aesthetically unattractive appearance. These problems include settling, migration and floatation of colorants in nail enamel, color drift in a face powder or blush cosmetic during wear, and staining of a lipstick on a person.

Despite the continuous efforts of the cosmetic industry to develop cosmetic compositions, especially nail enamels, that are more stable under normal use conditions, the appearance of the bottled nail enamel over time deteriorates rapidly leading to an aesthetically unattractive appearance of the product. Thus, the problem of instability remains unsolved for many nail enamel products.

To overcome the instability problem of nail enamels and to minimize or eliminate the aesthetic deterioration of certain cosmetics during normal use, the present invention provides nail enamel compositions that employ particulates, such as pigments, that are coated with fluorosilane.

Thus, the present invention provides a solution to the above problems by providing nail enamel compositions that are stable for an extended period of time, both in packaged form and after application, by maintaining the particulate materials, especially the pigments, dispersed and suspended in the composition. This further serves to maintain a truer color of the product because the settling of the pigments is prevented.

SUMMARY OF THE INVENTION

It is an object of the present invention to provide nail enamel compositions that have particulates, at least some of which, preferably most of which, are coated with fluorosilane.

It is another object of the present invention to provide a method for reducing settling, migration and floatation of colorants in a nail enamel, especially iron oxides and titanium dioxide.

It is still another object of the present invention to provide a method of reducing staining in a nail.

It is yet another object of the present invention to provide a method of increasing water resistance or repellency in a nail enamel.

It is a further object of the present invention to provide a method of improving gloss in a nail enamel.

It is still a further object of the present invention to provide a method of improving and/or increasing stability in a nail enamel.

It is yet a further object of the present invention to provide a method of improving wear of a nail enamel.

These and other objects will become more apparent with the benefit of the detailed description of the present invention, which includes a composition having particulates coated with fluorosilane, and a method of topically applying the composition to provide desired benefits.

DETAILED DESCRIPTION OF THE INVENTION

The present invention provides nail enamel compositions having particulates or particulate material coated with fluorosilane.

The term "fluorosilane" in the present invention refers to a silicon-containing compound having a hydrocarbyl group substituted by at least one fluorine atom and a reactive hydrocarbyloxy group capable of displacement by a nucleophile.

The term "hydrocarbyl" in the present invention refers to a linear, branched and cyclic group containing carbon and hydrogen, such as an alkane, an alkene, an alkyne and an aryl group. The hydrocarbyl group may be additionally interrupted and/or substituted by one or more of the following: a halogen, a cyano, a keto, an ester, hydroxyl, carboxyl, oxygen, sulfur, or nitrogen.

The term "perfluro hydrocarbyl" in the present invention refers to a fully fluorinated hydrocarbyl group.

The fluorosilane is represented by the formula:

$$R_fSi(OR)_3$$

wherein $R_f$ is a $C_4$–$C_{16}$ hydrocarbyl group having at least one fluorine atom, and wherein R is a $C_1$–$C_6$ hydrocarbyl group.

The preferred fluorosilane is represented by the formula:

$$R_f'CH_2CH_2Si(OR)_3$$

wherein $R_f'$ is a $C_4$–$C_{14}$ perfluoro hydrocarbyl group, and wherein R is methyl or ethyl.

An example of the preferred fluorosilane is tridecafluorooctyltriethoxy silane represented by the formula:

$$CF_3CF_2CF_2CF_2CF_2CF_2CH_2CH_2Si(OCH_2CH_3)_3$$

Tridecafluorooctyltriethoxy silane is available from Sivento, Piscataway, N.J., under the trade name DYNASILANE® F 8261.

The particulates coated with fluorosilane according to the present invention can be organic pigments, inorganic pigments, organic fillers, inorganic fillers, or any combination thereof. It is most important to coat the pigments.

Examples of the organic particulate pigments include azo, xanthene, quinone, lakes, especially aluminum lakes, strontium lakes, barium lakes, FD&C and D&C Red 6, Red 7, Red 30, Red 34, Yellow 5, Blue 1, derivatives thereof, and mixtures thereof. Examples of the inorganic particulate pigments are iron oxide, especially red and black iron oxides, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6 \cdot 3H_2O$), and mixtures thereof. Examples of the organic fillers include starch. Examples of the inorganic fillers include talc, mica, kaolin, silica, and mixtures thereof.

A preferred tridecafluorooctyltriethoxy silane-coated pigment includes tridecafluorooctyltriethoxy silane-coated black iron oxide, and tridecafluorooctyltriethoxy silane-coated red iron oxide.

The amount of fluorosilane is about 0.01 percentage by weight (wt %) to about 5 wt %, and the amount of particulates is about 95 wt % to about 99.99 wt %, of the total weight of the fluorosilane coated particulate. Preferably, the amount of fluorosilane is about 0.5 to about 2.0 wt %, and the amount of particulates is about 98 to about 99.5 wt % of the total weight of the fluorosilane coated particulate.

The particulates coated with fluorosilane are about 0.1 wt % to about 5.0 wt % of the total weight of the composition. Preferably, the particulates coated with fluorosilane are about 0.5 wt % to about 2.5 wt % of the total weight of the composition.

While, in general, the fluorosilane is about 0.0005 wt % to about 0.1 wt % of the total weight of the cosmetic composition, the amount of fluorosilane varies within the range depending upon its intended product. The fluorosilane is preferably about 0.01 wt % of the total weight in a nail enamel.

The compositions of the present invention can have a cosmetically acceptable vehicle. The vehicle can be or include ethanol, isopropanol, ethyl acetate, butyl acetate, nitrocellulose, a polyurethane, a polyamide, an acrylic polymer, an acrylic copolymer, or mixtures thereof.

Fluorine-treated particulates do not dissolve or disperse in water, hydrocarbon solvents or common organic solvents. Fluorosilanes are also insoluble in water and have limited solubility in hydrocarbon and other common organic solvents, but can sometimes be dispersed in ethanol or other fluoro polymers.

A nail enamel of the present invention can be prepared by dispersing particulate material, such as pigments and/or fillers coated with fluorosilane into a slurry. Such a slurry usually has about 20 wt % to about 40 wt % particulate material. The slurry is thereafter added to a nail enamel formulation.

It has now been surprisingly discovered that the benefits of the present invention can be achieved by the use of a nail enamel in which at least some of the particulates in the composition, particularly the pigments, are coated with fluorosilane. For example, by coating titanium dioxide with fluorosilane, reduced settling, migration and floatation of pigments occurs. Thus, less rheology modifiers, such as organoclays, are required to maintain good thixotropic properties. The benefit of using less rheology modifiers (i.e. less solids), is that the particulates in the nail enamel composition are decreased, whereby a "smoother" film (i.e. more even application) is realized. This further serves to enhance the gloss of the enamel.

Also, nail enamels containing pigments coated with fluorosilane exhibit a higher interfacial tension with water at ambient temperatures. The result of such high interfacial tension with water is that water is increasingly repelled and not absorbed into the nail enamel and, consequently, it is not able to swell the nail enamel. Thus, incorporation of pigments coated with fluorosilane into nail enamel compositions maintains and extends adhesion of the nail enamel film to the nail. The extended adhesion results in enhanced extended wear properties, including less chipping and scuffing.

This same high interfacial tension with water prevents the organic colorants, which have some water solubility, from interacting with moisture in the nail once surface treated. Thus, reduced nail staining is also achieved.

The present invention has been described with particular reference to the preferred embodiments thereof. It will be obvious that variations and modifications may be made therein without departing from the spirit and scope of the present invention as defined by the following claims. Also, singular used in the application can also mean plural of the same ingredient unless otherwise indicated. Furthermore, improving means increasing in performance, unless otherwise indicated.

Wherefore we claim:

1. A non-aqueous nail enamel composition comprising a plurality of particulates, wherein at least some of said plurality of particulates are coated with fluorosilane.

2. The composition according to claim 1, wherein said fluorosilane is represented by the formula:

wherein $R_f$ is a $C_4$–$C_{16}$ hydrocarbyl having at least one fluorine atom and R is a $C_1$–$C_6$ a hydrocarbyl.

3. The composition according to claim 2, wherein said fluorosilane is represented by the formula:

wherein $R_f'$ is a $C_4$–$C_{14}$ perfluoro hydrocarbyl and R is methyl or ethyl.

4. The composition according to claim 3, wherein said fluorosilane is represented by the formula:

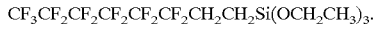

5. The composition according to claim 1, wherein said plurality of particulates are selected from the group consisting of pigments, fillers, and mixtures thereof.

6. The composition according to claim 5, wherein said pigment is selected from the group consisting of organic pigments, inorganic pigments, and a combination thereof.

7. The composition according to claim 6, wherein said pigment is an inorganic pigment selected from the group consisting of an iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6 \cdot 3H_2O$), and mixtures thereof, and wherein said filler is selected from the group consisting of mica, talc, silica, starch, and mixtures thereof.

8. The composition according to claim 1, further comprising a cosmetically acceptable vehicle.

9. The composition according to claim 1, wherein said particulates coated with fluorosilane are about 0.1 wt % to about 5 wt % of the total weight of the composition.

10. An unpigmented nail enamel composition comprising a fluorosilane.

11. A non-aqueous nail enamel composition comprising:
a non-aqueous cosmetically acceptable vehicle; and
a plurality of particulates; wherein at least some of said plurality of particulates are coated with fluorosilane, and wherein said fluorosilane is represented by the formula:

$$R_fSi(OR)_3$$

wherein $R_f$ is a $C_4$–$C_{16}$ hydrocarbyl having at least one fluorine atom and R is a $C_1$–$C_6$ a hydrocarbyl.

12. The composition according to claim 11, wherein said particulates coated with fluorosilane are about 0.1 wt % to about 5 wt % of the total weight of the composition.

13. The composition according to claim 12, wherein said particulates are selected from the group consisting of pigments, fillers, and mixtures thereof.

14. A method of reducing settling, migration and floatation of particulate colorants in a nail enamel, comprising coating at least some of said particulates with fluorosilane.

15. A method of reducing staining on a nail, comprising applying to said nail the composition of claim 1.

16. A method of improving water resistance in a non-aqueous nail enamel containing a plurality of particulates, comprising coating at least some of said plurality of particulates with fluorosilane.

17. A method of improving gloss of a non-aqueous nail enamel containing a plurality of particulates, comprising coating at least some of said plurality of particulates with fluorosilane.

18. A method of improving stability and rheology of a nail enamel, comprising making said nail enamel of the composition of claim 1.

19. A method of improving wear resistance of a non-aqueous nail enamel having a plurality of particulates, comprising coating at least some of said plurality of particulates with fluorosilane.

20. A method of providing a smooth and even application of nail enamel to a nail, comprising applying to said nail the composition of claim 1.

* * * * *

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

<u>Title page, Item [54] and Column 1, lines 1 and 2,</u>
Please amend the Title of the Invention to read:
-- NAIL ENAMEL COMPOSITION HAVING FLUOROSILANE COATED PARTICULATES --

<u>Column 6,</u>
Line 17, please add the following claims:

-- 21. The composition according to claim 1, wherein said at least some of said plurality of particulates coated with fluorosilane are present in an amount about 0.5 wt% to about 2.5 wt% based on the total weight of the composition.

22. The composition according to claim 1, wherein said fluorosilane is present in an amount about 0.0005 wt% to about 1 wt% based on the total weight of the composition.

23. The composition according to claim 10, wherein said fluorosilane is present in an amount about 0.1 wt% to about 5 wt% based on the total weight of the composition.

24. The composition according to claim 10, wherein said fluorosilane is represented by the formula:

$$R_f Si(OR)_3$$

wherein $R_f$ is a $C_4 - C_{16}$ hydrocarbyl having at least one fluorine atom and R is a $C_1 - C_6$ a hydrocarbyl.

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

25. The composition according to claim 10, wherein said fluorosilane is represented by the formula:

$$R_f'CH_2CH_2Si(OR)_3$$

wherein $R_f'$ is a $C_4 - C_{14}$ perfluoro hydrocarbyl and R is methyl or ethyl.

26. The composition according to claim 10, wherein said fluorosilane is represented by the formula:

$$CF_3CF_2CF_2CF_2CF_2CF_2CH_2CH_2Si(OCH_2CH_3)_3$$

27. A method of reducing staining on a nail, comprising applying to said nail the composition of claim 2.

28. A method of providing a smooth and even application of nail enamel to a nail, comprising applying to said nail the composition of claim 2.

29. A method of reducing staining on a nail, comprising applying to said nail the composition of claim 3.

30. A method of providing a smooth and even application of nail enamel to a nail, comprising applying to said nail the composition of claim 3.

31. A method of reducing staining on a nail, comprising applying to said nail the composition of claim 4.

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

32. A method of improving stability and rheology of a nail enamel, comprising making said nail enamel of the composition of claim 4.

33. A method of providing a smooth and even application of nail enamel to a nail, comprising applying to said nail the composition of claim 4.

34. The method according to claim 14, wherein said at least some of said particulates coated with fluorosilane are about 0.1 wt% to about 5 wt% based on the total weight of said nail enamel.

35. The method according to claim 14, wherein said fluorosilane is represented by the formula:

$$R_f Si(OR)_3$$

wherein $R_f$ is a $C_4 - C_{16}$ hydrocarbyl having at least one fluorine atom and R is a $C_1 - C_6$ a hydrocarbyl.

36. The method according to claim 14, wherein said fluorosilane is represented by the formula:

$$R_f' CH_2 CH_2 Si(OR)_3$$

37. The method according to claim 14, wherein said fluorosilane is represented by the formula:

$$CF_3 CF_2 CF_2 CF_2 CF_2 CF_2 CH_2 CH_2 Si(OCH_2 CH_3)_3$$

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

38. The method according to claim 37, wherein said at least some of said particulates are selected from the group consisting of iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6 \cdot 3H_2O$), mica, talc, silica, starch, and any mixtures thereof.

39. The method according to claim 16, wherein said at least some of said particulates coated with fluorosilane are about 0.1 wt% to about 5 wt% based on the total weight of said nail enamel.

40. The method according to claim 16, wherein said fluorosilane is represented by the formula:

$$R_fSi(OR)_3$$

wherein $R_f$ is a $C_4 - C_{16}$ hydrocarbyl having at least one fluorine atom and R is a $C_1 - C_6$ a hydrocarbyl.

41. The method according to claim 16, wherein said fluorosilane is represented by the formula:

$$R_f'CH_2CH_2Si(OR)_3$$

42. The method according to claim 16, wherein said fluorosilane is represented by the formula:

$$CF_3CF_2CF_2CF_2CF_2CF_2CH_2CH_2Si(OCH_2CH_3)_3$$

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

43. The method according to claim 42, wherein said at least some of said particulates are selected from the group consisting of iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6 \cdot 3H_2O$), mica, talc, silica, starch, and any mixtures thereof.

44. The method according to claim 17, wherein said at least some of said particulates coated with fluorosilane are about 0.1 wt% to about 5 wt% based on the total weight of said nail enamel.

45. The method according to claim 17, wherein said fluorosilane is represented by the formula:

$$R_fSi(OR)_3$$

wherein $R_f$ is a $C_4 - C_{16}$ hydrocarbyl having at least one fluorine atom and R is a $C_1 - C_6$ a hydrocarbyl.

46. The method according to claim 17, wherein said fluorosilane is represented by the formula:

$$R_f'CH_2CH_2Si(OR)_3$$

47. The method according to claim 17, wherein said fluorosilane is represented by the formula.

$$CF_3CF_2CF_2CF_2CF_2CF_2CH_2CH_2Si(OCH_2CH_3)_3$$

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

48. The method according to claim 47, wherein at least some of said particulates are selected from the group consisting of iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), mica, talc, silica, starch, and any mixtures thereof.

49. The method according to claim 19, wherein said at least some of said particulates coated with fluorosilane are about 0.1 wt% to about 5 wt% based on the total weight of said nail enamel.

50. The method according to claim 19, wherein said fluorosilane is represented by the formula:

$$R_fSi(OR)_3$$

wherein $R_f$ is a $C_4 - C_{16}$ hydrocarbyl having at least one fluorine atom and R is a $C_1 - C_6$ a hydrocarbyl.

51. The method according to claim 19, wherein said fluorosilane is represented by the formula:

$$R_f'CH_2CH_2Si(OR)_3$$

52. The method according to claim 19, wherein said fluorosilane is represented by the formula:

$$CF_3CF_2CF_2CF_2CF_2CF_2CH_2CH_2Si(OCH_2CH_3)_3$$

UNITED STATES PATENT AND TRADEMARK OFFICE
CERTIFICATE OF CORRECTION

PATENT NO. : 6,471,950 B1
DATED : October 29, 2002
INVENTOR(S) : Farer et al.

It is certified that error appears in the above-identified patent and that said Letters Patent is hereby corrected as shown below:

53. The method according to claim 52, wherein said at least some of said particulates are selected from the group consisting of iron oxide, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), mica, talc, si`lica, starch, and any mixtures thereof.

Signed and Sealed this

Twenty-second Day of April, 2003

JAMES E. ROGAN
*Director of the United States Patent and Trademark Office*